(12) United States Patent
Tan

(10) Patent No.: US 7,410,258 B2
(45) Date of Patent: Aug. 12, 2008

(54) METHOD AND APPARATUS FOR MONITORING GLAUCOMA USING SCANNING LASER TOMOGRAPHY

(76) Inventor: Chee Hian Tan, 3513 Lucia Crest, Madison, WI (US) 53705

( * ) Notice: Subject to any disclaimer, the term of this patent is extended or adjusted under 35 U.S.C. 154(b) by 369 days.

(21) Appl. No.: 11/056,905

(22) Filed: Feb. 11, 2005

(65) Prior Publication Data

US 2005/0180622 A1 Aug. 18, 2005

Related U.S. Application Data

(60) Provisional application No. 60/544,780, filed on Feb. 13, 2004.

(51) Int. Cl.
*A61B 3/00* (2006.01)
(52) U.S. Cl. ...................... 351/246; 382/128
(58) Field of Classification Search ................ 351/246, 351/212, 205, 206; 382/128
See application file for complete search history.

(56) References Cited

U.S. PATENT DOCUMENTS 3,622,323 A * 11/1971 Fraser ...................... 156/58
4,692,003 A * 9/1987 Adachi et al. ............. 351/212
2004/0254154 A1* 12/2004 Ashton ...................... 514/179

OTHER PUBLICATIONS

Lorraine Remer, Contouring and Topo Maps, Dec. 20, 2002, NASA, The Pumas Collection.*
Burke, Vihanninjoki, Bartke, Tuulonen, Airaksinen, Volcker, Konig□□ "Development of the Standard Reference Plane for the Heidelberg Retina Tomograph"□□2000, Springer-Verlag, No. 238, pp. 375-384.*
Tan, James C.H., et al., Reasons for Rim Area Variability in Scanning Laser Tomography, Investigative Opthalmology & Visual Science, Mar. 2003, vol. 44, No. 3 Association for Research in Vision and Opthalmology.
Tan, James C.H., et al., Reference Plane Definition and Reproducibility in Optic Nerve Head Images, Investigative Opthalmology & Visual Science, Mar. 2003, vol. 44, No. 3 Association for Research in Vision Opthalmology.
Tan, James C.H., et al., Validity of rim area measurements by different reference planes, United Kingdom.
Tan, James C.H., et al., Approach for Identifying Glaucomatous Optic Nerve Progression by Scanning Laser Tomography, Investigative Opthalmology & Visual Science, Mar. 2003, vol. 44, No. 6 Association for Research in Vision and Opthalmology.
Tan, James C.H., et al., Optimising and validating an approach for identifying glaucomatous change in optic nerve topography, United Kingdom.
Tan, C.H., et al., Tomographic identification of neuroretinal rim loss in high-pressure glaucoma, normal-pressure glaucoma and glaucoma suspects, United Kingdom.

* cited by examiner

*Primary Examiner*—Ricky L Mack
*Assistant Examiner*—James R Greece
(74) *Attorney, Agent, or Firm*—Boyle Fredrickson, S.C.

(57) ABSTRACT

A method of making reproducible and accurate longitudinal studies of neuroretinal rim area establishes a reference plane based on height values of a readily established contour line at the outer rim of the optic disc. The reference plane may be used to establish a second inner contour line, between which contour lines area is measured.

24 Claims, 12 Drawing Sheets

METHOD AND APPARATUS FOR MONITORING GLAUCOMA USING SCANNING LASER TOMOGRAPHY

CROSS-REFERENCE TO RELATED APPLICATIONS

This application claims the benefit of U.S. Provisional application 60/544,780 filed Feb. 13, 2004 hereby incorporated by reference.

STATEMENT REGARDING FEDERALLY SPONSORED RESEARCH OR DEVELOPMENT

--

BACKGROUND OF THE INVENTION

Glaucoma is a chronic eye disease in which nerve axons in the retina and optic nerve progressively die and vision is lost. The axonal loss progressively alters the topography of the optic disc and its surrounding retina. Treatment can control the progression of glaucoma, but inadequate treatment leaves the disease uncontrolled and can lead to blindness. It is thus important to be able to tell if the disease is progressing and if treatments are effective. Only monitoring over time will reveal the course of the disease.

To monitor glaucoma over time, sequential testing needs to be conducted over the course of disease to try to capture its changes. The period of testing is typically months to years, and measurements yielded by repeat testing over time are expected to have variability which can be significant and unpredictable. Glaucoma is known to evolve gradually, and relatively small changes due to the disease will have to be detected above measurement variability. As such, distinguishing true glaucoma-induced change from apparent change due to variability in these longitudinal measurements can be challenging.

The optic disc, the visible portion of the optic nerve, has two anatomical parts: a peripheral region called the neuroretinal rim (NRR) surrounds a central depression called the optic cup (cup). The NRR contains neural tissue, representing axons from the retina converging on the optic nerve to exit the eye. The cup is devoid of axons.

Change in the size of the NRR and cup serves as markers of disease progression. The size of the NRR and cup can be measured once the inner margin (inner rim) and outer margin of the NRR (outer rim) are defined in optic disc images. The outer rim forms the circumference of the optic disc, and is a fixed anatomical landmark and readily identifiable. The inner rim coincides with the edge of the cup and is defined as the region in which the NRR surface's flatter slope steepens maximally as it turns into the cup. It is more difficult to identify.

Identifying the location of the cup edge/inner rim is critical to evaluating the optic disc for disease progression. As axons are lost, it is the inner, not outer, rim that recedes as the NRR gets smaller and cup concurrently gets bigger. As the changes sought are on the most part relatively small, the inner margin needs to be identified reproducibly and accurately if such minute change is to be detected.

Conventionally, the area of the NRR (rim area) and cup (cup area) have been measured in stereoscopic optic disc photographs. But detecting the inner rim in these images relies on subjective interpretation such as perceiving subtle variations in color and contour, which compromises reproducibility.

A newer innovation is scanning laser tomography, an imaging method which yields digital topography images of the fundus for quantitative analysis. It has several advantages over photography. Contour lines can be marked on the outer rim in topography images and its coordinates saved to be exported to other images of the same eye. This same contour line location is automatically maintained throughout an image series. Another advantage is that topography images permit the use of alternative analytical approaches to objectively and automatically identify the inner rim.

One such approach is to position a reference plane in the topography of the optic disc being analyzed. However, the optic disc's topography normally differs considerably between persons and eyes, and how a reference plane should be positioned so that analysis is valid, reproducible and not biased by inter-individual differences has not been determined. While reference planes of various definitions have been proposed, none has been shown to consistently fit the wide range of optic disc topographies, nor yield measurements of the inner rim that are reproducible and accurate enough to be useful for monitoring change in the size of the NRR.

Finally, measurements derived from the repeated imaging of the same eye over time will almost certainly have variability that is easily mistaken for true change. If disease progression is to be discerned in longitudinal image series, there must be a way of reliably distinguishing true change due to disease from apparent change due to measurement variability.

BRIEF SUMMARY OF THE INVENTION

The present invention provides a robust method of fixing a reference plane that may be used for a variety of eye measurements over time, and that is largely free from operator bias, suitable for automation and applicable to a range of eye topographies.

Generally, the reference plane is fixed relative to a height derived from a readily established contour line such as the outer edge of the neuroretinal rim. This reference plane may then be accurately reestablished for subsequent longitudinal studies.

Specifically, the present invention provides a method of computer-assisted retina monitoring using topographic data of an optic disc of an eye. The method includes the steps of first defining a first contour line on the topographic data and then establishing a reference plane below the contour line fixed relative to a height of the contour line. The reference plane is then applied to the topographic data to define a second contour line at an inner neuroretinal rim and the area of the neuroretinal rim outside of the second contour line is measured.

It is thus one object of at least one embodiment of the invention to provide a method of accurately locating a reference plane over different images in a longitudinal study and applicable to a range of eye topographies.

The first contour line may be at an outer neuroretinal rim and the measuring may be between the first and second contour lines.

It is thus an object of at least one embodiment of the invention to use a contour line that is easily identified and at a location in the eye where minor variations in the tracing of this contour line will have little effect on the height of the reference plane. It is thus an object of at least one embodiment of the invention to provide a method suitable for the important measurement of neuroretinal rim area.

The reference plane may be defined with respect to a mean height of the first contour line.

It is another object of at least one embodiment of the invention to provide a robust height value that accommodates height irregularity in the eye surface at the contour line.

The reference plane may be a fixed distance below a mean height of the first contour line.

It is another object of at least one embodiment of the invention to provide a reference plane well suited to measurement of neuroretinal rim area.

The fixed distance may be a constant amount below lowest points of the first contour line applied to topographic data from a previous study of the eye.

It is another object of at least one embodiment of the invention to provide a method of locating the offset of the reference plane that may be automated.

The constant amount may be between 90 and 130 micrometers.

It is another object of at least one embodiment of the invention to provide a simple method of establishing the offset of the reference plane without undue calculation.

The fixed distance may be a distance providing least variability in area of the second contour line with incremental changes in the fixed distance as measured on earlier topographic data from a previous study of the eye or a representative group of eyes.

It is another object of at least one embodiment of the invention to provide an offset value that reduces artifacts in the area measurements caused by minor errors in the contour line placement The first contour line may be defined by a drawing by a physician on an image of the topographic data.

It is another object of at least one embodiment of the invention to provide a system that may accept manual input and yield a result that is resistant to interoperator variability.

The first contour line may be defined by a drawing by a physician on an image of earlier topographic data from a previous study of the eye.

It is another object of at least one embodiment of the invention to provide a system that requires and uses manual input only in the baseline study.

The measuring of the area of the neuroretinal rim may be made in angular sectors and the method may further include the step of outputting data showing the area of neuroretinal rim area as a function of angle for the topographic data. The data may also show measured area of neuroretinal rim area as a function of angle for earlier topographic data from a previous study of the eye.

It is another object of at least one embodiment of the invention to provide a measurement output that is sensitive to asymmetrical variations in neuroretinal area that otherwise might be masked.

The output data may also show a limit of variability below which no variation in area is meaningful.

It is another object of at least one embodiment of the invention to provide a physician or researcher with a clear indication of when variation is significant.

These objects will not be realized by all embodiments of the invention. For this reason, the objects should not be considered as limiting the scope of the invention. The scope of the invention should be determined by reference to the claims. A preferred embodiment is also described. The preferred embodiment is not exhaustive of all practical embodiments of the invention nor is it intended to be. For this reason, again, the claims should be consulted to determine the scope of the invention.

DETAILED DESCRIPTION OF THE INVENTION

The following is a description of a method to analyze the topography of the optic disc in sequential topographic images to identify change. The method incorporates 1) an analytical reference plane that optimizes measurement reproducibility, 2) a statistical method for estimating and accounting for measurement variability in longitudinal data so that change exceeding variability may be identified, 3) an approach for interpreting and verifying change in a way that is clinically meaningful.

Scanning Laser Tomography of the Optic Disc

Scanning laser tomography is a well-established technique for imaging structures in the living eye, typically of the retina and optic disc. The device is a type of confocal microscope that takes images in sections through an object of interest in a way analogous to CT scanning. This involves acquiring a sequence of images at equally-spaced optical planes through the depth of the retinal object in a single pass taking a few seconds.

Figure 1:
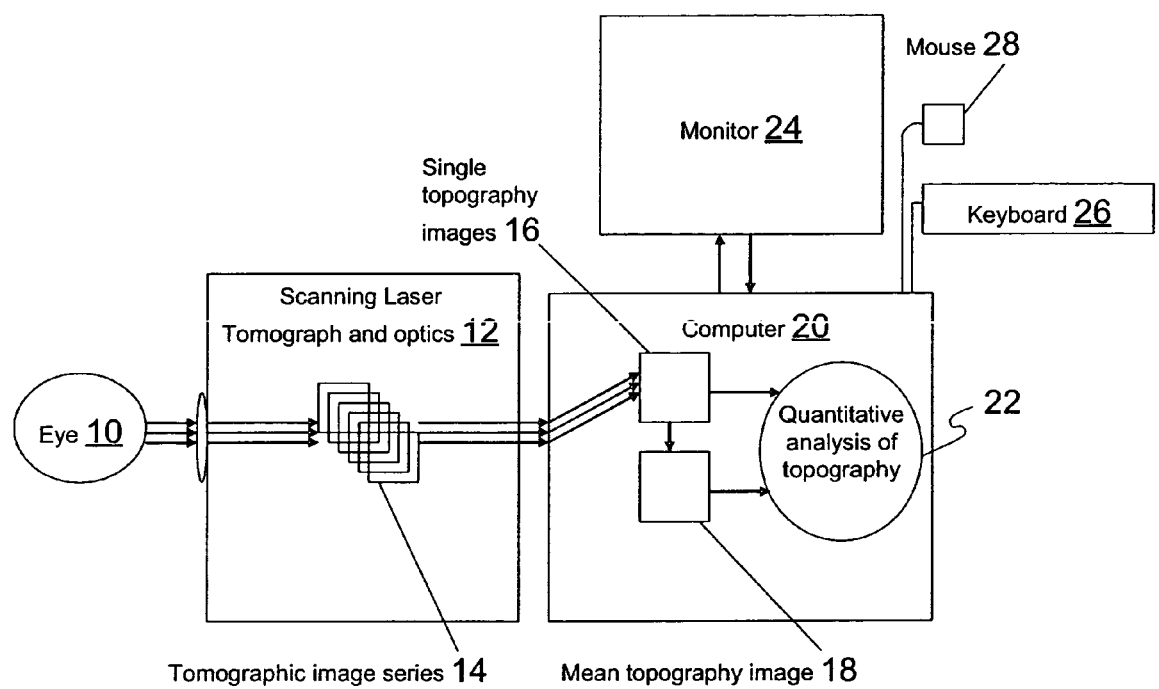
FIG. 1 is a schematic of the apparatus and steps for acquiring and processing the images of scanning laser tomography.

FIG. 1 describes the components of the apparatus and steps required to capture and generate a topography image. The fundus of the eye 10 is imaged through its pupil using the scanning laser tomograph 12. This yields a tomographic image series 14 containing data that can be processed to generate topography images. Topography images, of which there are two kinds: single 16 and mean 18, are the final and key outputs of the image acquisition and processing. They contain the essential data describing surface topography. The image acquisition hardware is controlled by software in a computer 20 which also has features for image processing to generate the topography images, and for rudimentary quantitative analysis of topographical data 22. An examiner monitors and directs the imaging process aided by a computer screen 24, keyboard 26 and mouse 28.

Figure 2:
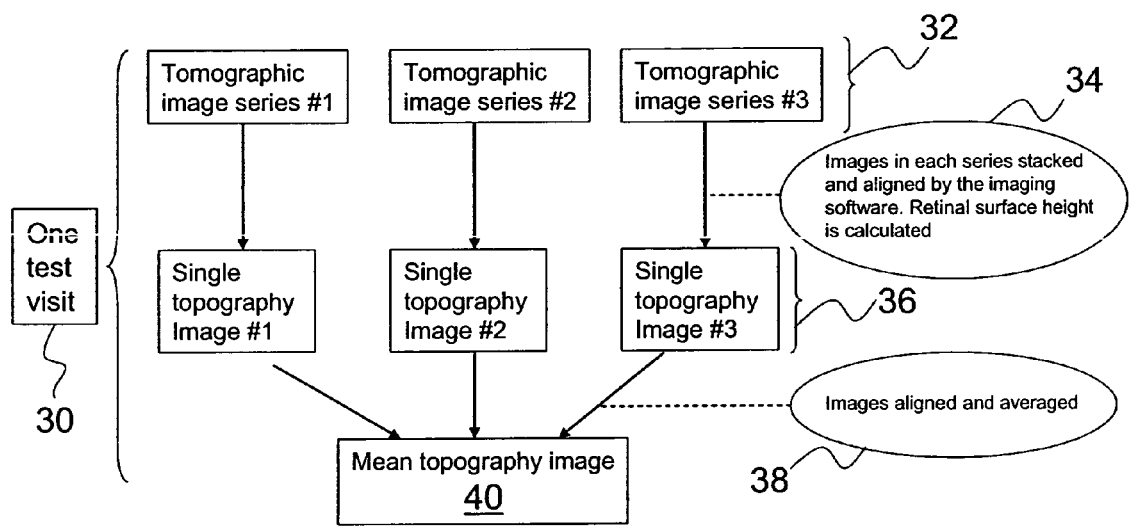
FIG. 2 is a diagram summarizing the steps to generate single and mean topography images.

FIG. 2 summarizes the steps to derive single and mean topography images. A topography image is a digital matrix of pixels (e.g., 256×256 on an x- and y-axis grid), each carrying a value representing height on the topographical z-axis at that pixel location. During a test visit Process block 30, several, typically three, sets of tomographic image series Process block 32 are acquired of the same eye. Each tomographic image series is stacked and aligned in register by the software Process block 34 to construct a composite image called a single topography image Process block 36. The single topography images from the same test visit are aligned by the imaging software and their data is averaged Process block 38 to generate a mean topography image 40. Mean topography images contain averaged height data from corresponding pixel locations of multiple single topography images from a common test visit; this aside, the appearance and nature of the topographical data in both image types is the same.

Figure 3:
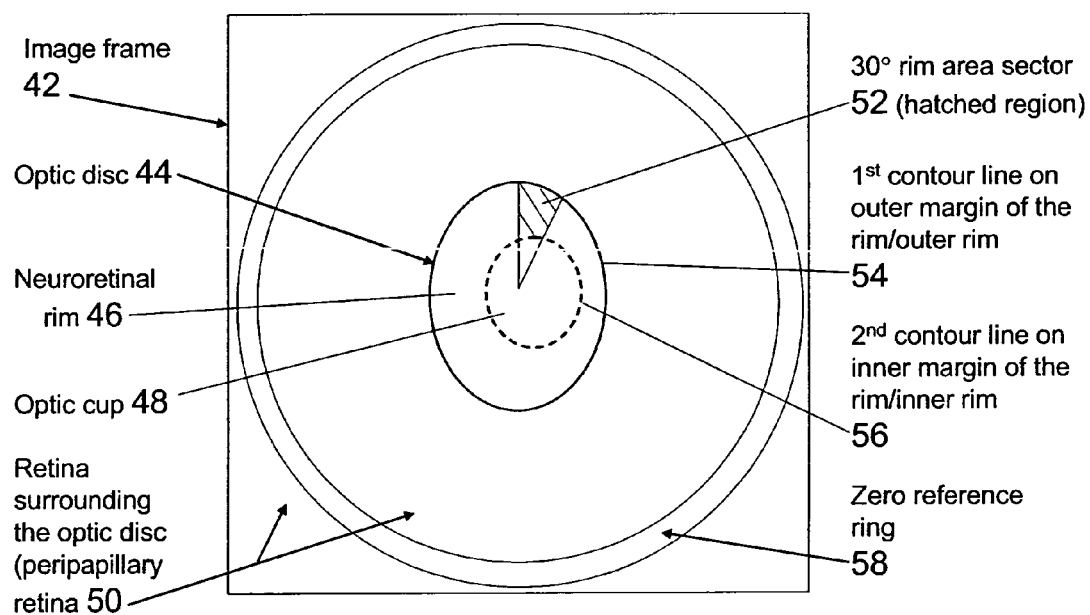
FIG. 3 is a schematic of a topography image of the optic disc showing features of its anatomy and the location of the zero-reference region.

FIG. 3 illustrates a topography image bounded by an image frame 42. In the centre of the frame is the optic disc 44 divided into two anatomical parts, the NRR 46 and cup 48. Surrounding the optic disc and extending to the image frame is the retina (peripapillary retina) 50. During software analysis of this image, the size of the NRR can be measured wholly and/or in sectors 52 once the outer margin (outer rim) 54 and inner margin (inner rim) 56 of the NRR have respectively been indicated by the 1st and 2nd contour lines. The inner and outer rims correspond to the boundaries of the optic cup and optic disc respectively. An observer marks the 1st contour line along the circumference of the outer rim with a mouse while viewing the computer monitor. The coordinates of the 1st contour line's location are saved in the imaging software as specific to an optic disc, and then exported to other images of the same optic disc to preserve the 1st contour line's position in the image series. The location of the inner rim, as indicated by the 2nd contour line, is defined by an analytical tool called a reference plane. Once the location of both contour lines is known, the size of the NRR and cup can be measured.

The zero-reference ring 58 is centered on the image frame, located in the image periphery of the peripapillary retina, and has an outer diameter 94% and width 3% of the size of the image frame. It is an arbitrary zero-reference region that is well-accepted for calculating the location of zero on the topographical z-axis in topography images. The average of all the pixel height values within an image's zero-reference ring is taken to be the level of topographical zero specific to that image. The topographical height value at each pixel location in an image is the height of the retinal surface relative to the image's own topographical zero. While this definition of topographical zero is used for the method described herein, the method also accepts the use of alternative definitions.

Method for Monitoring Glaucoma in Topography Images
Reference Plane Analysis

Figure 4:
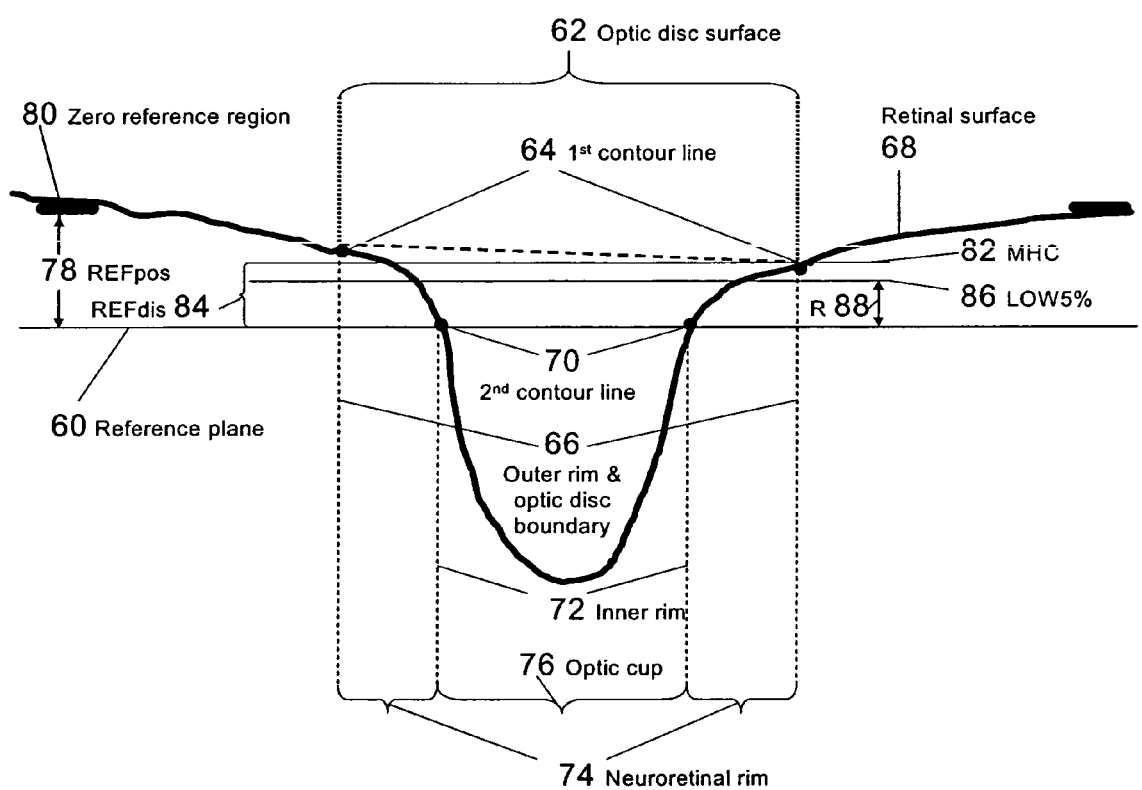
FIG. 4 is a cross-sectional diagram of the topography of the optic disc illustrating its characterization by a reference plane, and parameters for positioning the reference plane in topography.

FIG. 4 shows analysis of the optic disc's topography by a reference plane 60. The imaging software defines the optic disc region 62 as the surface enclosed by the 1st contour line 64 marking the outer rim and optic disc boundary 66. The surface outside the optic disc boundary is that of the retina 68. The reference plane lies roughly parallel to and below the plane of the peripapillary retina. It intersects the topography of the optic disc to define the location of the 2nd contour line 70 marking the inner rim 72. The NRR 74 is that surface enclosed by the 1st contour line but lying above the reference plane; this is the surface lying between the 2nd contour line marking the inner rim and the 1st contour line. The cup 76 is the surface enclosed by the 1st contour line but lying below the reference plane; this is the surface enclosed within the 2nd contour line. By this method, various dimensions of the NRR and cup (e.g., height, area, volume) can be analyzed. The following description will deal only with the analysis of rim area.

Position of the reference plane in topography is critical: too low and the size of the NRR is overestimated, too high and the NRR is underestimated; conversely the size of the cup is respectively underestimated and overestimated. Changes from image to image of the reference plane's position relative to optic disc features being measured causes measurement variability. The reference plane should ideally: 1) lie lower than the 1st contour line marking the outer rim, which is the optic disc's boundary, 2) lie at the level of the true inner rim marked by the 2nd contour line, which was defined earlier as the region in which the flatter slope of the rim surface steepens maximally as it turns into the cup, and 3) retain its z-axis position relative to the optic disc irrespective of topographical variation arising from imaging variability, or change due to disease.

The position of the reference plane on the topographical z-axis (REFpos) 78 with respect to the topographical zero 80 is described by the equation:

$$REFpos = MHC + REFdis \qquad \text{[equation 1]}$$

MHC (Mean Height of the Contour line) 82 is the mean of topographical height at pixel locations along the 1st contour line and represents the optic disc's position on the z-axis. This value is calculated by the imaging software. REFdis 84 is the z-axis distance of the reference plane below MHC and is unique to each optic disc and all its topography images. While MHC will vary from image to image, once REFdis is calculated in the baseline test visit, it is held constant throughout an image series; this significantly reduces rim area variability. REFdis can be calculated once LOW5% and R are known.

$$REFdis = LOW5\% + R \qquad \text{[equation 2]}$$

Thus, REFpos can also be described as:

$$REFpos = MHC + LOW5\% + R \qquad \text{[equation 3]}$$

LOW5% 86 is a topographical height value derived from 5% of the lowest locations on the contour line. It defines a level above which the reference plane should not rise, as should the reference plane come to lie above LOW5%, it will misclassify parts of the optic disc and NRR as absent. Topographical height at locations 1° apart (360 values) on the outer rim (1st contour line) of single topography images (typically three) from the baseline test visit are determined from the imaging software. These height values are ranked and the mean of the lowest 5% of values is calculated for each image. Finally, the mean values of the 5% lowest heights of each of the single topography images are averaged to give LOW5%.

R 88 is the z-axis distance of the reference plane beneath LOW5% where the variability in rim area measurements (rim area variability) is least. This ensures that the position of the reference plane: 1) is at a fixed distance and wholly beneath the circumference of the outer rim, 2) is at a level where rim area variability is least, and 3) tends toward the level of the inner rim, where rim area variability is expected to be less than with the reference plane located more superficially in the NRR. To determine R, rim area variability has been assessed for different reference plane depths in topography images of normal control optic discs and found to lie between 90-130 micrometers. Alternatively, R for a particular eye can be determined by repeating the foregoing analysis of variability for different references plane depths in single topography images of that eye's baseline test visit. This customizes R to the topography of an optic disc so that the value of R is specific to that eye.

Data from all single and mean topography images from all test visits is used to analyze the NRR for change: mean topography images provide the point-estimates for rim area, while single topography images provide the data for estimating rim area variability.

Figure 5:
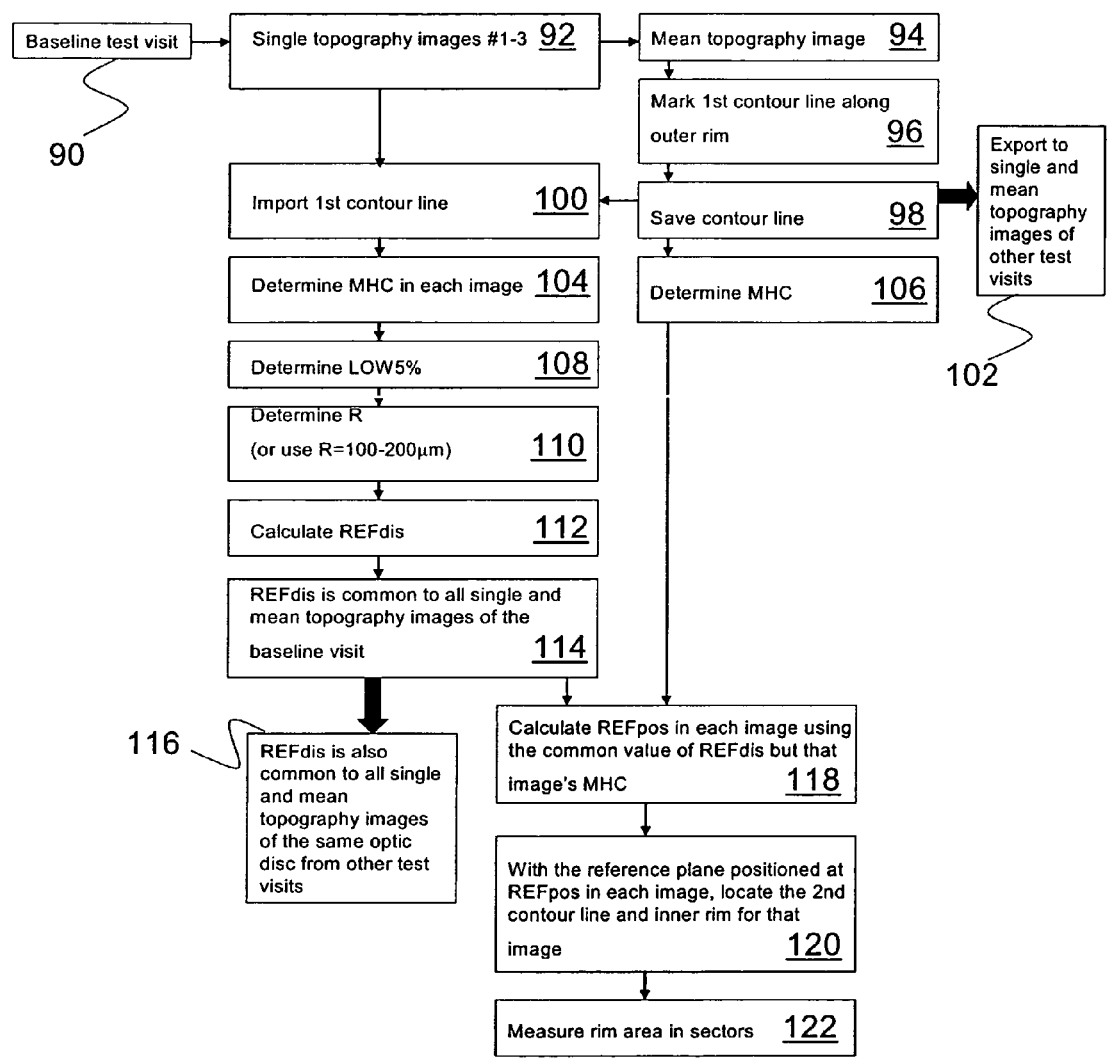
FIG. 5 is a flowchart for positioning the reference plane in single and mean topography images of the baseline test visit to measure rim area.

FIG. 5 summarizes steps to position the reference plane in topography to analyze rim area in sequential images acquired over sequential test visits. One test visit is designated the baseline test visit Process block 90. Single 92, then mean 94 topography images are generated from tomography image series acquired at that baseline test visit. One of these topography images, usually the mean topography image, is selected to have the 1st contour line 96 marked on the optic disc's outer rim. This position is saved 98 and becomes the common position of the 1st contour line for all images of the same optic disc. The 1st contour line is exported to all other images from the baseline test visit 100. The same saved position is also exported to single and mean topography images from other test visits Process block 102. In the baseline test visit, MHC is now determined in each of the single topography images 104 and the mean topography image 106. LOW5% 108 and R 110 are then calculated in the single topography images. A value for R can also be obtained by analyzing a group of images of different optic discs; this has been found to be in the range of 90-130 micrometers. REFdis 112 is then derived according to Equation 2. The derived value of REFdis from the baseline visit is used to calculate REFpos in all single and mean topography images of the baseline test visit 114 and other test visits Process block 116 according to Equation 1. In the baseline visit, REFpos can now be determined for each single and mean topography image 118 using each image's MHC value but the common value of REFdis. With the reference plane positioned at REFpos, the location of the 2nd contour line 120 marking the inner rim is known. With the locations of the inner and outer rims known, rim area can be analyzed in 30° sectors 122. Sectors measurements are necessary as glaucoma may damage the optic disc very locally in a way that might be missed if rim area is not measured in small enough parts. To display the data, the sectors are ordered by angular location around the circumference of the optic disc so that the location of each sector is easily identifiable.

Figure 6:
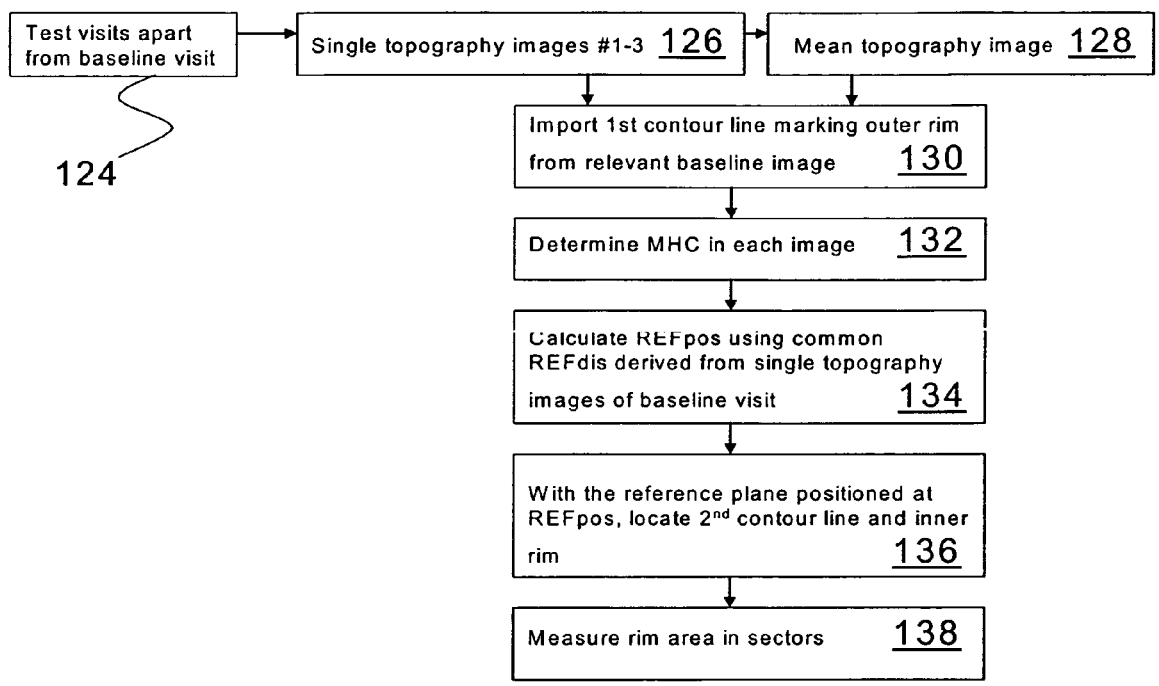
FIG. 6 is a flowchart for positioning the reference plane in single and mean topography images of the non-baseline test visit to measure rim area.

FIG. 6 summarizes steps to analyze single and mean topography images from test visits other than the baseline test visit Process block 124. Single 126, then mean 128 topography images are generated from tomography image series acquired at each of these test visits. Both image types are analyzed in the same way. The 1st contour line for these images is imported from the relevant topography image from the baseline test visit 130; thus the position of the 1st contour line is preserved throughout the image series. MHC 132 is then determined in each image. To calculate REFpos 134 in an image, the common REFdis value derived in the baseline test visit's topography images is added to that image's value of MHC according to Equation 1. With the reference plane positioned at REFpos 136, the location of the 2nd contour line and inner rim is known. Rim area in 30° sectors can now be measured 138.

2) Estimating Rim Area Variability in Sectors

Measurement variability imposes a limit on how small change can be before it becomes undetectable above 'noise'. If rim area measurements are observed to be changing over time, a decision needs to be made as to whether the observed change is consistent with the disease process or measurement variability. To distinguish between real change and variability, rim area variability first needs to be estimated. Meaningful change attributable to disease would then be defined as that change exceeding variability.

Rim area variability in each sector of the optic disc within an image series is estimated by calculating each sector's statistical limits of variability. Each sector's limits define the range of values over which observed change in a sector is statistically attributable to variability. It can be considered a measure of agreement between repeat measurements of the same sector. Expressed differently, the limits of variability define the smallest amount of change that can be expected to be detected above measurement variability.

Each sector's limits of variability are calculated from estimates of how much the sector's rim area measurements vary between single topography images taken during the same test visit. The single topography images from the same visit are used to calculate intra-visit rim area sector difference estimates' or 'δ', which is the difference in the rim area of corresponding sectors in pairs of same-visit single topography images.

Figure 7:
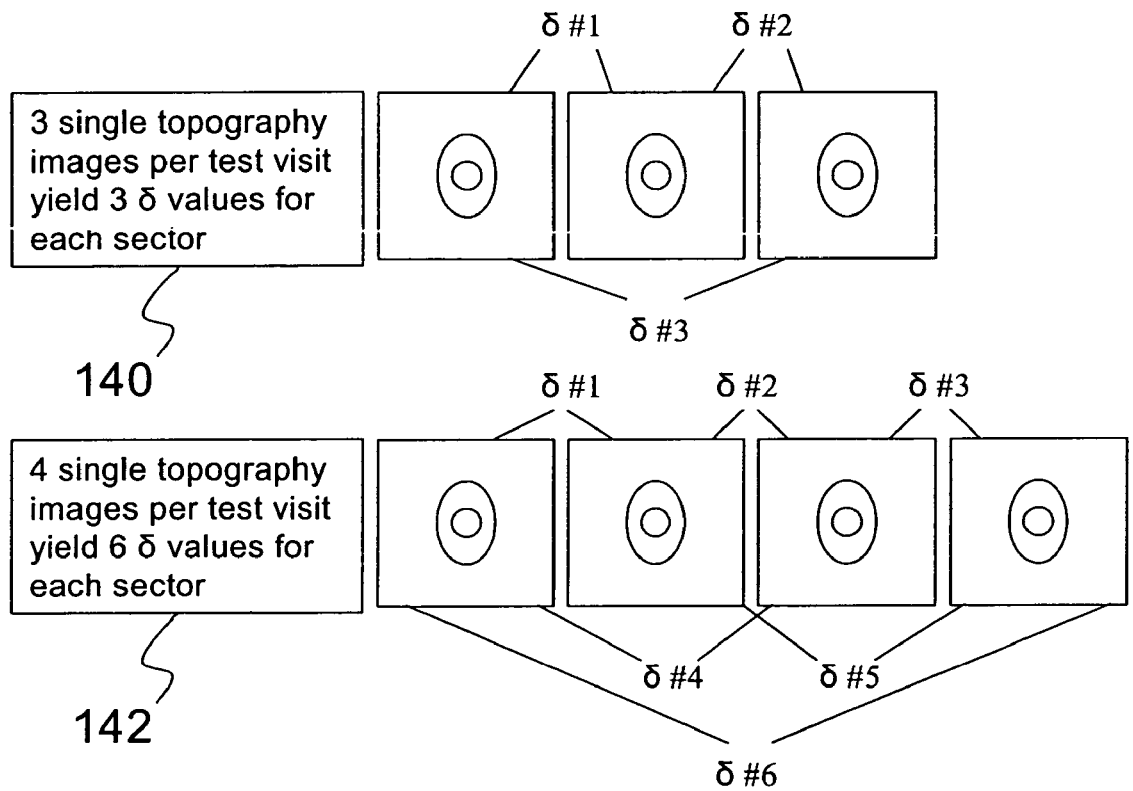
FIG. 7: Diagram illustrating how the number of single topography images per test visit influences the number of δ values calculated in that visit.

FIG. 7 shows examples of test visits at which an eye is imaged different numbers of times. Typically, the optic disc is imaged three times at a test visit to yield three single topography images per visit. From these images, three δ values are derived for each sector Process block 140. But the more images acquired per visit, the greater the number of δ values for that visit: hence, four intra-visit images yield six δ values per visit for each sector Process block 142, five images per visit yield 10 δ values, six images per visit yield 15 δ values and so on according to the equation:

$$^{m}C_{r}=m!/(m-r)!r!$$ [equation 4]

Where $^{m}C_{r}$ is the number of combinations of δ per test visit, m is the number of single topography images from a visit that can be combined to calculate δ, and r is the number of images used in each combination (r=2).

Figure 8:
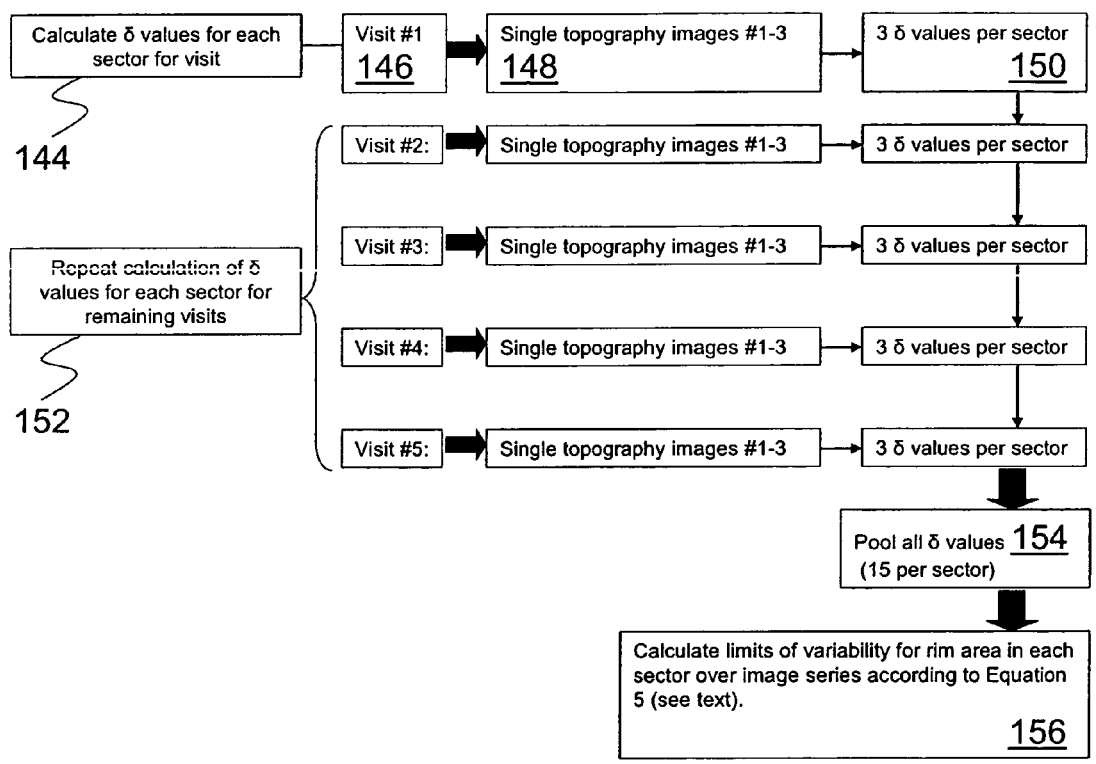
FIG. 8: Diagram summarizing the steps to derive and pool δ values from sequential test visits to calculate the limits of variability.

FIG. 8 illustrates the steps to derive limits of variability for each sector. Values of δ have first to be calculated for each sector Process block 144 in images acquired in the first test visit 146. Several single topography images (typically three) 148 are generated from the tomographic image series acquired during that test visit. The multiple single topography images provide the data by which each sector's δ values for that test visit are calculated 150. This analysis is repeated at each test visit to yield a number of δ values per visit for each sector Process block 152. The δ values from across all test visits are pooled 154 to derive the limits of variability (VARLIM) for each sector over the image series 156 according to the equation:

$$VARLIMa=Y^{*}\sqrt{\Sigma(\delta_{i}-X)^{2}/(n-1)}$$ [equation 5]

Where, a=sector number (corresponding to the order of a 30° sector's location on the optic disc circumference between 0-360°), δ=sector rim area difference between pairs of intra-visit single topography images, i=ith value of δ, X=mean of observations of δ, and n=number of observations of δ. Y=value of the t-statistic for degrees of freedom for δ, corresponding to a chosen two-tailed probability value such as p=0.05.

The limits of variability are the confidence limits for each sector's range of δ values, calculated by multiplying the standard deviation of δ by the appropriate point of the t-distribution for n−1 degrees of freedom. This allows for better estimates of the limits of variability when dealing with relatively small samples (say of less than 60, which is typical for this type of data). The number of δ values in any image series equates the total of all δ values from all visits; all are used to calculate the limits of variability. The estimation of variability is dynamic and changes as an image series grows so that the limits of variability can be expected to narrow with increasing degrees of freedom for δ.

The value of δ is taken to be free from change due to disease, being derived from data from within a test visit on a single day, not between visits. The preceding analysis assumes that the values of δ for each sector have a Gaussian distribution, which can be expected in most sectors due to the way in which differences tend to be distributed. To ensure that the data is normally distributed, the distribution of δ in each sector is checked using histograms, normal plots and Shappiro-Wilk W significance testing. Any departures from normality are transformed using a transformation such as: $\ln(X^2)$. Following transformation where needed, δ is expected to be normally distributed within image series. This checking for distributions and the transformation of data can be automated in software.

3) Interpreting Longitudinal Data

Figure 9:
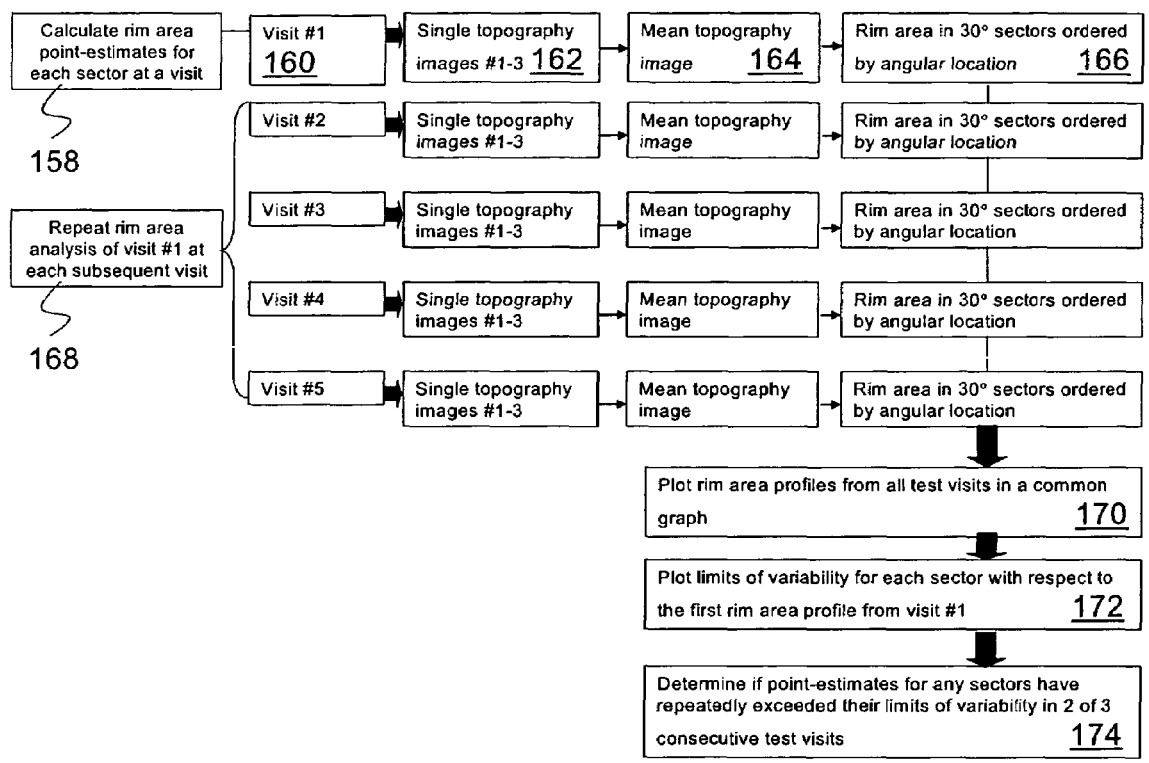
FIG. 9 is a diagram summarizing the steps to derive rim area point-estimates for each sector, and their analysis with respect to the limits of variability.

With reference to FIG. 9, the mean topography image for a test visit provides the point-estimate of rim area for that visit Process block 158; that is, each point-estimate is a measure of rim area at a separate time-point. At the first test visit 160, single topography images 162, which are derived from tomographic image series acquired at that visit, are used to generate a mean topography image 164. The point-estimates of rim area in 30° sectors are derived from mean topography images, and ordered by angular location around the optic disc 166. The calculation of point-estimates of rim area sectors performed for the first test visit is repeated for image data from all other test visits Process block 168. Different point-estimates for rim area are plotted as separate rim area profiles in a common graph 170. The limits of variability for each sector are plotted with respect to the first rim area profile 172, which is the earliest measurement time-point in an image series. To ascertain if there is change in an image series, rim area profiles subsequent to the first rim area profile are assessed to determine if any of their sectors have changed relative to the first point-estimate in time to exceed their respective limits of sector variability 174. If change is observed in at least one sector in 2 of 3 consecutive tests, the optic disc meets the criterion for repeatable and verified change. This change is considered significant. True change, unlike random variability, is expected to be consistent and therefore repeatable. If the lower limits of variability are exceeded to meet the criterion for repeatability, the change is taken to represent glaucoma progression.

Figure 10:
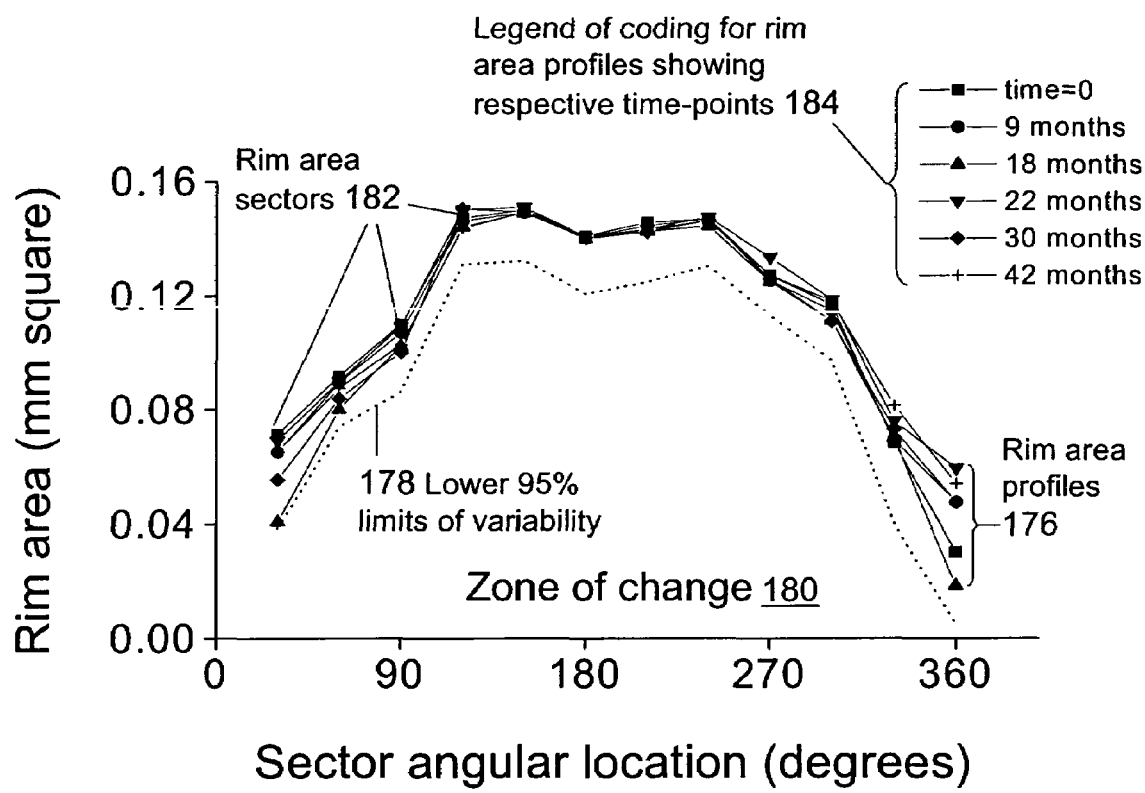
FIG. 10 is an example of a normal optic disc in which the analysis of sequential rim area profiles by lower 95% limits of variability indicates the absence of glaucoma progression.

FIG. 10 shows an example of sequential rim area profiles 176 from the image series of a normal optic disc, plotted with respect to lower 95% limits of variability 178. The lower limits of variability border the zone of change 180, which lies beneath these limits. For each graph, rim area profiles are plots of sector rim area 182 by each sector's angular location on the circumference of the optic disc (0-360°, with 0°=temporal, 90°=superior, 180°=nasal, 270°=inferior) from the same image series. Rim area profiles are coded (e.g., by symbol or color) to represent their different time-points and interpreted with the help of a legend 184. The plot of sequential rim area profiles shows that no sectors have decreased relative to the first time-point to exceed their lower limits of variability and enter the zone of change. This indicates that no glaucoma progression is detected. Variation seen in the positions of sequential rim area profiles is due to measurement variability and not disease.

Figure 11:
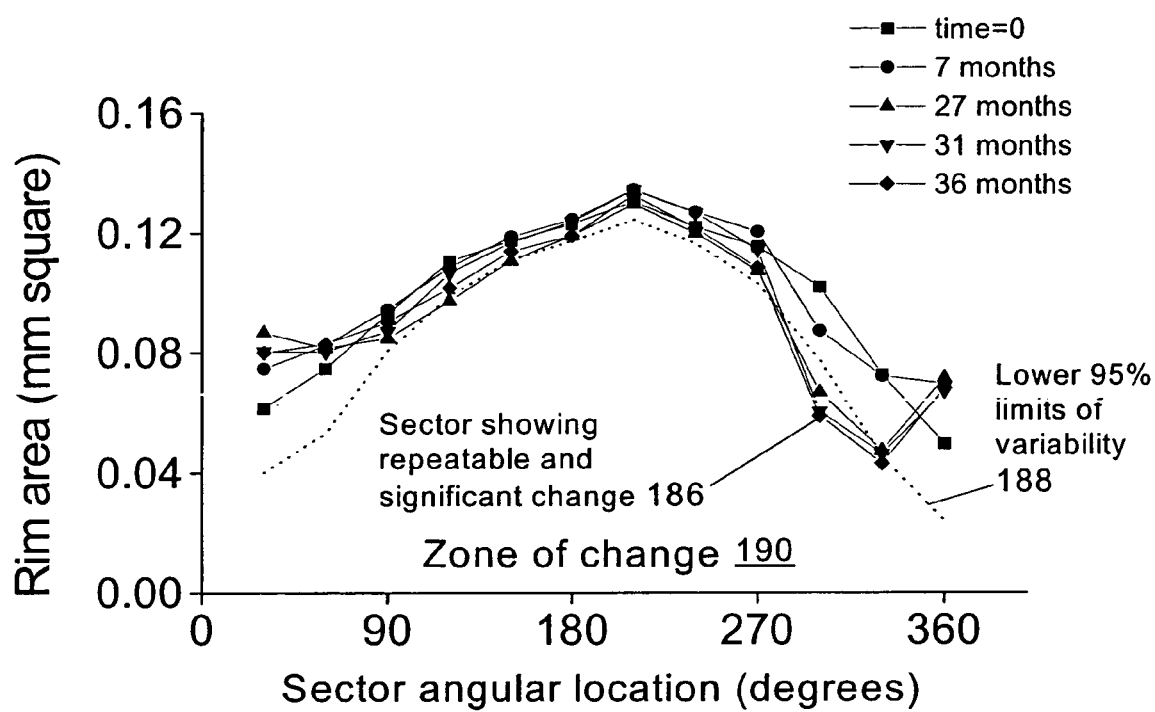
FIG. 11 is an example of an optic disc with glaucoma in which the analysis of sequential rim area profiles with respect to lower 95% limits of variability demonstrates localized glaucoma progression.

FIG. 11 shows an example of an optic disc with localized glaucoma progression. There is significant and repeatable localized change wherein one sector 186 has exceeded the lower 95% limit of variability 188 to enter the zone of change 190 in 3 of 3 consecutive test visits. This meets the criterion requiring that change be verified in at least 2 of 3 consecutive test visits, and represents glaucoma progression.

Figure 12:
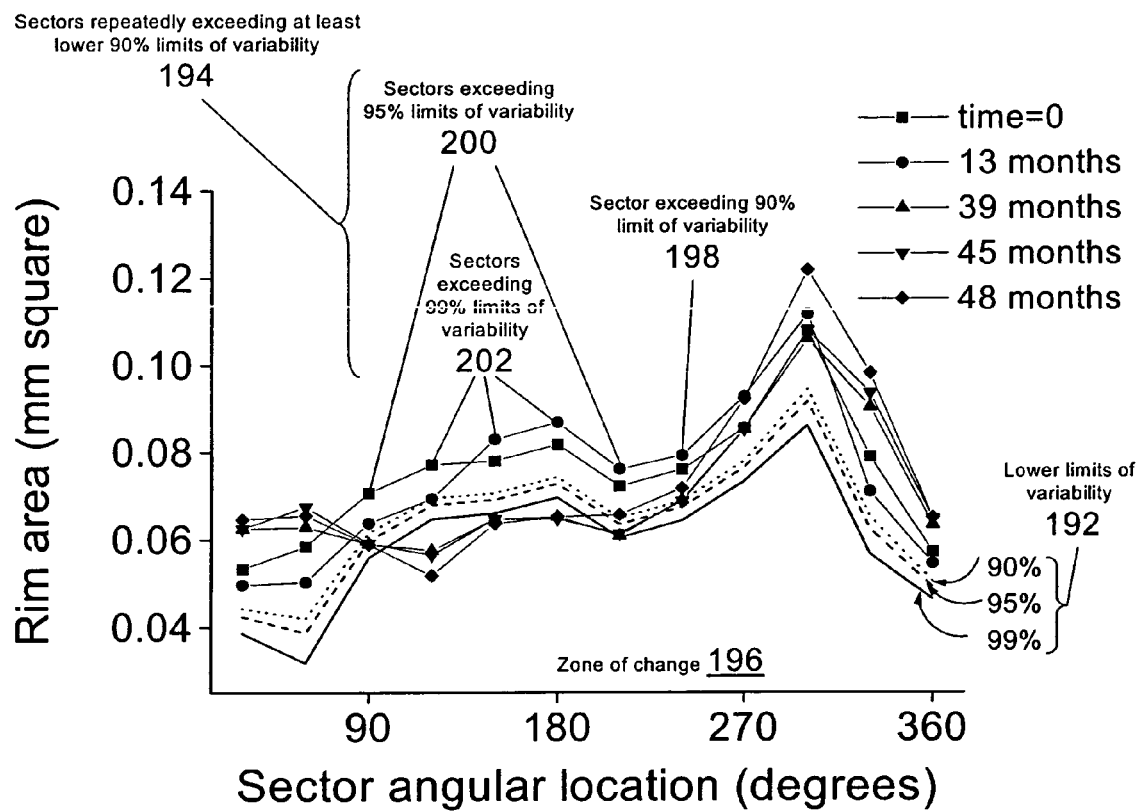
FIG. 12 is an example of an optic disc with glaucoma in which the analysis of sequential rim area profiles with respect to multiple limits of variability demonstrates widespread glaucoma progression.

FIG. 12 shows an example of an optic disc with widespread glaucoma progression. Rim area profiles are plotted with respect to various statistical lower limits of variability representing lower 90%, 95% and 99% confidence limits for variability 192 in the same graph. Six sectors have exceeded at least their lower 90% limits of variability repeatedly 194 to enter the zone of change 196: one sector has exceeded its lower 90% limit of variability 198, two sectors have exceeded their lower 95% limits of variability 200, and three sectors have exceeded their lower 99% limits of variability 202 in at least 2 of 3 consecutive test visits. The stricter the statistical limit exceeded (e.g., 99% compared with 90%), the higher the probability that change represents true change due to disease and not apparent change due to measurement variability. Change in all six sectors can be verified as meeting the criterion for repeatable change, indicating the presence of significant and widespread glaucoma progression. Assessing rim area profiles by multiple limits of variability yields extra useful information that can help guide clinical decisions.

The examiner views a computer monitor on which the analytical output of sequential rim area profiles and limits of variability are displayed next to the series of mean topography images by which the rim area profiles are derived. The images are ordered sequentially and labeled with their date of acquisition. Three forms of the same image series are displayed simultaneously: 1) topography images as they appear prior to contour line and reference plane analysis; 2) the same topography images as (1) but with the entire space within the boundary of the 1st and 2nd contour lines color-coded to indicate the region of the NRR analyzed; and 3) the same topography images as (1) but with color-coding confined to the 30° NRR sectors that have met the criterion for significant and repeatable change. This provides a comprehensive pictorial depiction of the NRR with respect to the graphical analysis at each time-point in a way that allows the longitudinal data to be weighed both quantitatively and qualitatively. The examiner can also thus verify if the quantitative analysis of change agrees with the appearance of the NRR as seen in the images.

The converse of an increase in the size of the NRR is sometimes observed after glaucoma treatment. In the analysis described, such an occurrence is manifest as an elevation in the position of parts or all of a rim area profile relative to time-points prior to treatment. To determine if such elevation represents a significant increase in rim area, sequential rim area profiles are analyzed with respect to their upper instead of lower limits of variability. These upper limits are calculated as described in Equation 5. If the upper limits are exceeded to meet the criterion for repeatable change, then the change observed is attributed to the effect of treatment.

A concomitant change in cup size accompanies any change in the size of the NRR, and this too can be assessed by the described method. Cup area, for example, can be measured once the inner rim is identified by reference plane analysis. Sector cup area is then evaluated for significant and repeatable change with respect to each cup sector's area limits of variability along the same lines as described for rim area. Likewise, with appropriate adaptation, the foregoing methodology can be applied to identify change in other aspects of topography such as the volume and height/depression of the NRR, optic cup or retina.

It is specifically intended that the present invention not be limited to the embodiments and illustrations contained herein, but that modified forms of those embodiments including portions of the embodiments and combinations of elements of different embodiments also be included as comes within the scope of the following claims.

I claim:

1. A method of computer assisted monitoring using topographic data of the optic disc of an eye comprising the steps of:

(a) defining a first contour line on the topographic data;

(b) establishing a reference plane below the contour line fixed relative to a height of the contour line; wherein the reference plane is a fixed distance below a mean height of the first contour line; wherein the fixed distance is a constant amount below lowest points of the first contour line applied to topographic data from a previous study of the eye;

(c) applying the reference plane to the topographic data to define a second contour line at an inner neuroretinal rim; and (d) measuring an area of the optic disc with respect to the second contour line;

(e) outputting the measure of the area of the optic disc.

2. The method of claim 1 wherein the first contour line is at an outer neuroretinal rim and the measuring of step (d) is at least one of an area measurement between the first and second contour lines and within the second contour line.

3. The method of claim 1 wherein the reference plane is defined with respect to a mean height of the first contour line.

4. The method of claim 1 wherein the constant amount is between 90 and 130 micrometers.

5. The method of claim 1 wherein the fixed distance is a distance providing least variability in area of the second contour line with incremental changes in the fixed distance as measured on earlier topographic data from a previous study of the eye.

6. The method of claim 1 wherein the first contour line is defined by a drawing by a physician on an image of the topographic data.

7. The method of claim 1 wherein the first contour line is defined by a drawing by a physician on an image of earlier topographic data from a previous study of the eye.

8. The method of claim 1 wherein the measuring of the area of the optic disc is made in angular sectors and further including the step of outputting data showing the area of at least one of the neuroretinal rim and optic cup as a function of angle for the topographic data.

9. The method of claim 1 wherein the data also shows measured area of at least one of the neuroretinal rim and optic cup as a function of angle for earlier topographic data from a previous study of the eye.

10. The method of claim 1 wherein the data also shows a limit of variability beyond which no variation in area is meaningful.

11. The method of claim 1 wherein the topographic data is a composite of several measurements of the eye.

12. The method of claim 1 wherein steps (a)-(e) are repeated for topographic data from a single measurement of the eye and a composite of several measurements of the eye.

13. A computer program embodied in a computer readable medium executable on a computer for glaucoma monitoring using topographic data of the optic disc of an eye and executable on an electronic computer to:

(a) accept data defining a first contour line on the topographic data;

(b) establish a reference plane below the contour line fixed relative to a height of the contour line; wherein the reference plane is a fixed distance below a mean height of the first contour line; wherein the fixed distance is a constant amount below lowest points of the first contour line applied to topographic data from a previous study of the eye;

(c) apply the reference plane to the topographic data to define a second contour line at an inner neuroretinal rim; and (d) measure an area of the optic disc with respect to the second contour line;

(e) output the measure of the area of the optic disc to a clinician.

14. The computer program embodied in a computer readable medium executable on a computer of claim 13 wherein the first contour line is at an outer neuroretinal rim and the measuring of step (d) is at least one of an area measurement between the first and second contour lines and within the second contour line.

15. The computer program embodied in a computer readable medium executable on a computer of claim 13 wherein the reference plane is defined with respect to a mean height of the first contour line.

16. The computer program embodied in a computer readable medium executable on a computer of claim 13 wherein the constant amount is between 90 and 130 micrometers.

17. The computer program embodied in a computer readable medium executable on a computer of claim 13 wherein the fixed distance is a distance providing least variability in area of the second contour line with incremental changes in the fixed distance as measured on earlier topographic data from a previous study of the eye.

18. The computer program embodied in a computer readable medium executable on a computer of claim 13 wherein the first contour line is defined by a drawing by a physician on an image of the topographic data.

19. The computer program embodied in a computer readable medium executable on a computer of claim 13 wherein the first contour line is defined by a drawing by a physician on an image of earlier topographic data from a previous study of the eye.

20. The computer program embodied in a computer readable medium executable on a computer of claim 13 wherein the measuring of the area of the optic disc is made in angular sectors and further including the step of outputting data showing the area of at least one of the neuroretinal rim and optic cup as a function of angle for the topographic data.

21. The computer program embodied in a computer readable medium executable on a computer of claim 13 wherein the data also shows the measured area of at least one of the neuroretinal rim and optic cup as a function of angle for earlier topographic data from a previous study of the eye.

22. The computer program embodied in a computer readable medium executable on a computer of claim 13 wherein the data also shows a limit of variability beyond which no variation in area is meaningful.

23. The computer program embodied in a computer readable medium executable on a computer of claim 13 wherein the topographic data is a composite of several measurements of the eye.

24. The computer program embodied in a computer readable medium executable on a computer of claim 13 wherein steps (a)-(e) are repeated for topographic data from a single measurement of the eye and a composite of several measurements of the eye.

* * * * *